(12) United States Patent     (10) Patent No.:   US 12,685,500 B2
Fischer et al.     (45) Date of Patent:     Jul. 21, 2026

(54) DETECTOR FOR A POSITRON EMISSION TOMOGRAPHY (PET)-SCANNING DEVICE

(71) Applicant: Positrigo AG, Zürich (CH)

(72) Inventors: Jannis Nikolaus Rudolf Fischer, Zürich (CH); Max Ludwig Ahnen, Zürich (CH)

(73) Assignee: Positrigo AG, Zurich (CH)

( * ) Notice: Subject to any disclaimer, the term of this patent is extended or adjusted under 35 U.S.C. 154(b) by 18 days.

(21) Appl. No.: 18/699,639

(22) PCT Filed: Nov. 1, 2022

(86) PCT No.: PCT/EP2022/080397
§ 371 (c)(1),
(2) Date: Apr. 9, 2024

(87) PCT Pub. No.: WO2023/078842
PCT Pub. Date: May 11, 2023

(65) Prior Publication Data
US 2024/0324976 A1     Oct. 3, 2024

(30) Foreign Application Priority Data
Nov. 8, 2021    (EP) .................................... 21206834

(51) Int. Cl.
*A61B 6/42*     (2024.01)
*A61B 6/03*     (2006.01)
(Continued)

(52) U.S. Cl.
CPC ............ *A61B 6/4275* (2013.01); *A61B 6/037* (2013.01); *A61B 6/4266* (2013.01); *A61B 6/501* (2013.01); *A61B 6/0478* (2013.01)

(58) Field of Classification Search
CPC ..... A61B 6/4275; A61B 6/037; A61B 6/4266; A61B 6/501; A61B 6/0478; A61B 6/4258
See application file for complete search history.

(56) References Cited

U.S. PATENT DOCUMENTS 7,209,579 B1 *   4/2007   Weisenberger ...... A61B 6/5247
                                382/128
10,634,747 B2    4/2020   Majewski et al.
(Continued)

FOREIGN PATENT DOCUMENTS

CN     113476070 A    10/2021
DE     3022360 A1    1/1981
(Continued)

OTHER PUBLICATIONS

International Search Report issued Feb. 10, 2023 in International Application No. PCT/EP2022/080397.
(Continued)

*Primary Examiner* — Sean D Mattson
(74) *Attorney, Agent, or Firm* — Sughrue Mion, PLLC

(57) ABSTRACT

A detector (2) for a positron emission tomography (PET)-scanning device is provided, the detector (2) including an opening (28) sized to accommodate the head of a human patient (P) and a plurality of sensor modules (22), which serve to detect emitted PET-radiation from the human patient (P) and which are arranged in the form of a regular polygon having a plurality of corners (24a, 24b, 24c). The detector further has an inner surface (23), which is arranged radially inside of the sensor modules (22), in order to circumferentially delimit the opening (28). The sensor modules (22) are arranged such that one of the corners is a nose corner (24a) which is adapted to accommodate the patient's nose (N) in the intended normal use of the detector (2). The inner surface (23) reflects the shape of the polygon at least in the region of the nose corner (24a).

11 Claims, 4 Drawing Sheets

(51) Int. Cl.
   *A61B 6/50*   (2024.01)
   *A61B 6/04*   (2006.01)

(56)          References Cited

U.S. PATENT DOCUMENTS

| | | | |
|---|---|---|---|
| 2004/0097800 | A1 | 5/2004 | Crosetto |
| 2004/0232348 | A1* | 11/2004 | Beekman .............. G01T 1/2985 |
| | | | 250/393 |
| 2006/0261276 | A1* | 11/2006 | Muehllehner ......... G01T 1/2985 |
| | | | 250/363.05 |
| 2010/0288935 | A1* | 11/2010 | Majewski ................. G01T 1/00 |
| | | | 250/363.03 |
| 2012/0324648 | A1* | 12/2012 | Amano ................ A61B 6/4482 |
| | | | 5/601 |
| 2016/0166219 | A1* | 6/2016 | Majewski .............. A61B 6/501 |
| | | | 250/362 |
| 2018/0204327 | A1* | 7/2018 | Matthews ............ A61B 5/7275 |

FOREIGN PATENT DOCUMENTS

| | | |
|---|---|---|
| EP | 3 449 834 A1 | 3/2019 |
| WO | 02/093195 A2 | 11/2002 |

OTHER PUBLICATIONS

Xu et al., "Progresses in Designing a High-sensitivity Dodecahedral PET for Brain Imaging", 2016 IEEE Nuclear Science Symposium, Medical Imaging Conference and Room-Temperature Semiconductor Detector Workshop (NSS/MIC/RTSD), Oct. 29, 2016, 2 pages total.

Catana, "Development of Dedicated Brain PET Imaging Devices: Recent Advances and Future Perspectives", The Journal of Nuclear Medicine, Aug. 2019, vol. 60, No. 8, pp. 1044-1052.

Melroy et al., "Development and Design of Next-Generation Head-Mounted Ambulatory Microdose Positron-Emission Tomography (AM-PET) System", Sensors, 2017, vol. 17, No. 5, pp. 1-15.

* cited by examiner

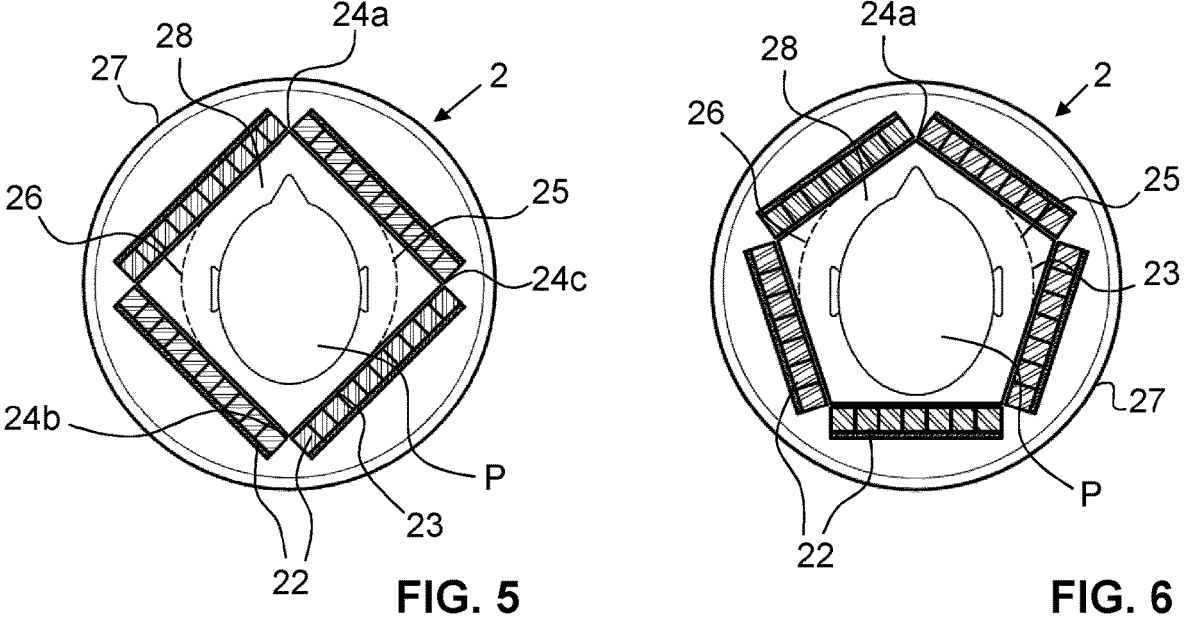
FIG. 5                      FIG. 6
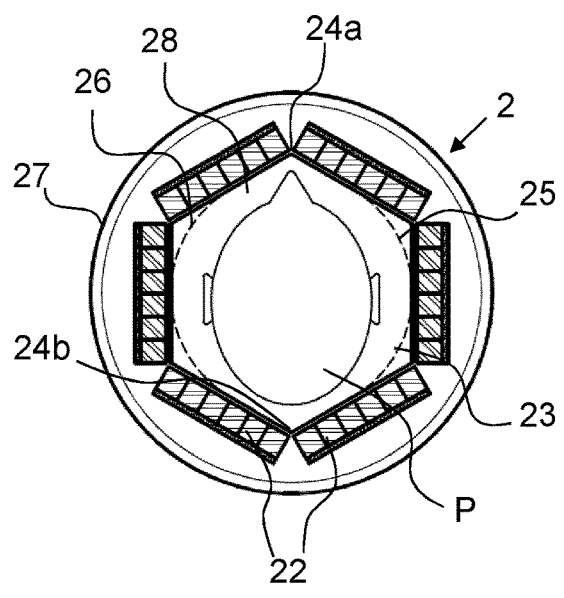
FIG. 7

DETECTOR FOR A POSITRON EMISSION TOMOGRAPHY (PET)-SCANNING DEVICE

CROSS REFERENCE TO RELATED APPLICATIONS

This application is a National Stage of International Application No. PCT/EP2022/080397 filed Nov. 1, 2022, claiming priority based on European Patent Application Ser. No. 21/206,834.0 filed Nov. 8, 2021.

TECHNICAL FIELD

The present invention relates to a detector for a positron emission tomography (PET)-scanning device, which is adapted to detect PET-radiation emitted from the head of a human patient.

PRIOR ART

Positron emission tomography (PET)-scanning devices are usually in the form of whole body-scanners with a large bore to fit an entire human body. If, however, e.g. only the head or one of the extremities of a human patient is of interest with regard to the PET-imaging, then the wide bore of a whole body-scanner is disadvantageous, because it requires the sensor modules of the detector to be located further away from the region-of-interest. Positioning the sensor modules at a greater distance from the region to be imaged reduces the sensitivity and specificity of the PET-scanning device.

Furthermore, whole body-scanners are usually big and bulky and only available at hospitals or at dedicated radiology facilities. As a consequence, patients have to travel to the place of the PET-scanning device, in order to be scanned, if required. The patients, however, are often elderly or sick people who live in a nursing home, cannot move well or are confined to bed. As a result, the travel to the PET-scanning location is cumbersome for the patients and often involves a not inconsiderable risk that the patient may have a complication while traveling or becomes infected, for example. Thus, most state of the art PET-scanning machines have the drawback that they cannot be brought to subjects.

A whole body PET-scanning device is for example disclosed in DE 30 22 360 A1. The device comprises a plurality of detector modules for detecting emitted PET-radiation that are arranged in a hexagon.

WO 02/093195 A2 discloses an apparatus for obtaining tomographic images. The apparatus comprises a detector with an octagonal inner surface.

A large portion of PET-scanning is related to the imaging of the human brain. For this purpose, however, a whole body PET-scanner with a large bore to fit the entire human body is often used. This means that disadvantages in terms of sensitivity and specificity have to be accepted and that the PET-scanning device cannot be brought to the patients.

A new generation of PET-scanning devices in the form of small-sized brain scanners has recently entered the market. US 2016/0166219 A1 is directed to a device that combines a virtual reality system with PET-brain imaging. A mobile brain imager is suspended on a mobile support which can be carried in the form of a backpack or which can be arranged on a carriage having wheels. The device comprises a detector ring that is slightly oval in cross-sectional view and has a plurality of sensor modules.

A PET-scanner that is geometrically adaptable to the part of the patient to be imaged is disclosed by US 2004/0097800 A1.

EP 3 449 834 A1 proposes a PET-brain scanner with a detector that has a helmet-like design with a plurality of flat detector modules.

SUMMARY OF THE INVENTION

It is an object of the present invention to provide a detector for a positron emission tomography (PET)-scanning device which is particularly well adapted for human brain imaging.

In order to achieve this object, the present invention provides a detector for a positron emission tomography (PET)-scanning device, the detector comprising an opening sized to accommodate the head of a human patient;

a plurality of sensor modules, which serve to detect emitted PET-radiation from the human patient and are arranged in the form of a regular polygon having a plurality of corners; and an inner surface, which is arranged radially inside of the sensor modules, in order to circumferentially delimit the opening.

The sensor modules are arranged such that one of the corners is a nose corner which is adapted to accommodate the patient's nose in the intended normal use of the detector. The inner surface reflects the shape of the polygon at least in the region of the nose corner.

An arrangement of the sensor modules in the form of a regular polygon is optimal in particular with regard to the post processing of the acquired PET-data. Due to the regular arrangement, each of the sensor modules can basically be treated in the same way in the post processing and in particular in the tomographic reconstruction, which is not the case, if the sensor modules are arranged in the form of an irregular polygon, such as e.g. a polygon having an oval shape. Thus, with an arrangement of the sensor modules in the form of a regular polygon, data post processing can be greatly facilitated.

By arranging one of the polygon's corners in the immediate region of the patient's nose and, thus, in such a way, that it is adapted to accommodate the patient's nose, the space of the detector's opening can be optimally used for the scanning of a human head or, in other words, the sensor modules can be positioned closer to the head of the patient. Thus, the nose, which itself forms a corner of the human head, can be accommodated in a corner of the regular polygon formed by the sensor modules. The advantage of arranging one of the polygon's corners in the immediate region of the patient's nose is particularly pronounced with a polygon that has a small number of corners. By arranging the sensor modules closer to the head, the sensitivity of the detector can be increased, which can be used to improve image quality and/or to reduce the radioactive dose for the patient and/or to reduce scanning time.

The PET-scanning device is preferably particularly adapted for brain scanning. The PET-scanning device can in this case be referred to as a brain PET-scanning device. For this purpose, the polygon formed by the sensor modules preferably has an incircle with a diameter of 220 to 300 mm, more preferably of 240 to 280 mm, in particular of approximately 260 mm. Of course, even if it the device is particularly adapted for a brain PET-scanning, the device can usually also be used for other purposes, such as e.g. the scanning of human extremities or for animal or plant scanning.

The detector is preferably in the form of a detector ring, meaning that it is closed along the circumferential direction. By forming a closed ring, the sensors can be optimally arranged along the entire inner surface of the detector. A closed ring also maximizes the detector sensitivity.

A regular polygon is a polygon that is equiangular, i.e. all corners of the polygon have the same opening angles, and equilateral, i.e. all sides of the polygon have the same length.

The sensor modules are preferably all of identical design. Preferably, the sensor modules all have a flat design, meaning that at least their surface facing towards the detector's opening is flat in each case. They are advantageously arranged immediately next to each other along the incircle of the detector polygon, i.e. along the circumference of the detector.

The inner surface is usually formed by a housing of the detector, which accommodates the sensor modules. Thus, the inner surface serves to separate the opening and, thus, the patient's head, from the sensor modules.

At least because it reflects the shape of the polygon in the region of the nose corner, the inner surface has an unround, i.e. non-circular, design. It is well possible, however, that the detector, in particular the detector's housing, has an outer surface with a round design. The shape of the polygon is reflected by the inner surface in the region of the nose corner, if in a cross-sectional (i.e. transversal) view of the detector, the inner surface forms a corner in the immediate area of the polygon's nose corner. The corner can be slightly rounded, as long as it is still well recognizable as a corner with respect to the entire cross-section of the inner surface. The corner formed by the inner surface preferably has an opening angle that differs from the opening angle of each of the polygon's corners by not more than 10°, more preferably by not more than 5°. In a particularly preferred embodiment, the corner formed by the inner surface in the immediate region of the patient's nose has the same opening angle as the polygon's corners.

By reflecting the shape of the inner surface at least in the region of the nose corner, the nose corner is reproduced by the inner surface in respect of both position and shape. In other words, the shape of the inner surface corresponds to the shape of the polygon in the region of the nose corner. Thus, the inner surface forms a corner which is adapted to accommodate the patient's nose in the intended use of the detector.

For accommodating the nose of the patient, the corner formed by the inner surface at the position of the nose corner preferably has an opening angle of less than 150°, more preferably of less than 140°.

In a particularly preferred embodiment, the polygon, which is formed by the arrangement of the sensor modules, has twelve corners or less. If there are more than twelve corners, the effects associated with the adaptation of the detector to the human head are considerably reduced. However, with twelve corners or less, significant advantages can be achieved in terms of detector sensitivity.

On the other hand, with a larger number of sensor modules that are arranged in the form of a polygon having four corners or more, in particular five corners or more, a better sensitivity can be achieved, particularly if it is considered that the patient usually does not fill the detector's opening completely.

Taking into account the considerations above, an optimum can be found of an arrangement having at least five and not more than twelve corners, in particular not more than eight corners.

Preferably, the inner surface also reflects the shape of the polygon in a region which is arranged diametrically opposite of the nose corner. In this way, the space of the opening to accommodate the usual elongate transversal shape of the human head can be maximized.

Particularly preferred can be an arrangement of the sensor modules in such a way that a polygon is formed which has an even number of corners. With an even number of corners, there is a corner which is arranged diametrically opposite of the nose corner, i.e. directly at the back of the head in the intended use of the PET-scanning device. The corner at the back of the head is then preferably reproduced by the inner surface in respect of both position and shape, meaning that the inner surface likewise forms a corner which is positioned directly at the back of the head in the intended use of the PET-scanning device. The provision of a corner at the back of the head can be used for positioning the patient's head centrally within the detector's opening. For example, the corner can be used as a guidance line or to accommodate a headrest. As a consequence, the corner arranged diametrically opposite of the nose corner can also be referred to as a headrest corner. Moreover, due to the slightly elongated shape of the human head in the transversal view, the provision of a corner at the back of the head is advantageous for accommodating the head and, thus, to adapt the detector to the head.

In other embodiments, however, it can also be advantageous to have an arrangement of the sensor modules in such a way that a polygon is formed which has an uneven number of corners. In this case, the inner surface can be flat in the region that is diametrically opposite of the nose corner, which can for example be advantageous for accommodating a headrest.

In a particularly preferred embodiment, the polygon is an octagon. It has turned out that the shape of an octagon, i.e. of a regular octagon, is particularly advantageous, because it does not only have corners in the immediate regions of the nose and back of the head, but also in the immediate regions of the ears. The provision of corners at the ears is usually not only perceived as convenient by the patient, but also brings about the advantage that they offer space at an optimal position of the detector for accommodating a device to support patient positioning. The device to support patient positioning can particularly be in the form of one or several laser positioning devices. A laser positioning device projects a line onto the patient, which helps the operator of the PET-scanner to correctly position the patient's head with respect to the detector, e.g. based on the patient's canthomeatal line.

Thus, independently of the number of corners of the polygon, the inner surface preferably also reflects the shape of the polygon in the immediate regions where the ears of the patient are arranged in the intended normal use of the detector.

In the areas of some of the plurality of corners, the inner surface can describe a curvature that corresponds to the incircle of the polygon. In this way, the inner surface has a particularly smooth and rounded design in the areas, where the additional space of the corners is not needed. The incircle is a term known from geometry and is considered to be the largest circle contained in the polygon.

In a particularly advantageous embodiment, the polygon is an octagon and the inner surface describes a curvature that corresponds to the incircle of the octagon in the areas of every second of the plurality of corners, starting with a corner being arranged adjacent to the nose corner. In the corner that is diametrically opposite of the nose corner, i.e. in the headrest corner, the inner surface preferably also forms a corner. Such an octagonal shape with an inner surface that follows the incircle in at least four corners has turned out to be particularly advantageous, both in terms of detector sensitivity and patient comfort.

Embodiments are particularly possible, in which the inner surface reflects the shape of the polygon along of its entire circumference. In other words, the inner surface also has the shape of a regular polygon. If the inner surface has the same shape as the arrangement of the sensor modules, the space of the detector's opening can be maximized.

Preferably, one sensor module is assigned to each side of the polygon. In other embodiments, it would of course also be possible that two or an integral multiple of sensor modules is assigned to each side of the polygon.

The invention is also directed to a positron emission tomography (PET)-scanning device comprising a detector as indicated.

The PET-scanning device can have a main supporting structure to which the detector is attached. The detector can particularly be attached to a main supporting structure in such a way that it can be translationally displaced along e.g. a guide rail of the main supporting structure. The patient can then be in a sitting or lying position during the PET-imaging and the detector can be (fine-) positioned optimally with respect to the patient without having to move the patient.

The PET-scanning device can comprise a headrest that serves for accommodating the head of the patient during the PET-imaging. For this purpose, the headrest is preferably adapted to be accommodated within the opening of the detector diametrically opposite of the nose corner.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 5 shows a schematic cross-sectional view through the detector of a PET-scanning device according to a second inventive embodiment, with a patient's head accommodated in the detector's opening;

FIG. 6 shows a schematic cross-sectional view through the detector of a PET-scanning device according to a third inventive embodiment, with a patient's head accommodated in the detector's opening;

FIG. 7 shows a schematic cross-sectional view through the detector of a PET-scanning device according to a fourth inventive embodiment, with a patient's head accommodated in the detector's opening;

DESCRIPTION OF PREFERRED EMBODIMENTS

Figures 1, 2:
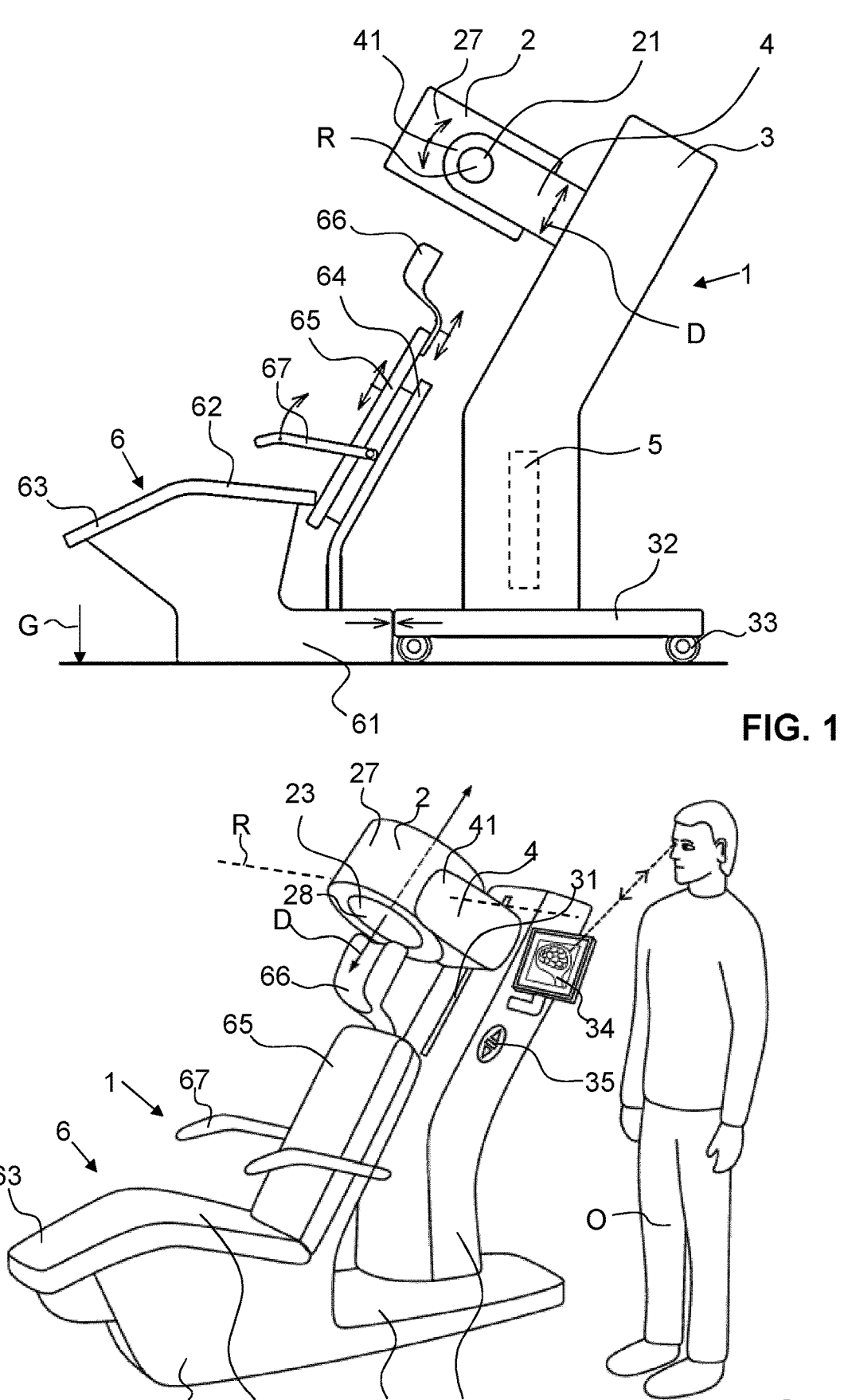
FIG. 1 shows a schematic side view of a first variant of an inventive PET-scanning device.
FIG. 2 shows a schematic perspective view of a second variant of an inventive PET-scanning device together with an operator.

In FIGS. 1 to 9, several different embodiments of a PET-scanning device 1 and/or a detector 2 are shown. Elements that have the same or a similar function, but belong to different embodiments, are annotated with the same reference numerals in each case.

In both embodiments as shown in FIGS. 1 and 2, the PET-scanning device 1 comprises a detector in the form of a detector ring 2, which has a plurality of sensor modules arranged along of its inner surface 23. The inner surface 23 radially delimits an opening 28 of the detector ring 2. The sensor modules, which are not visible in FIGS. 1 and 2, serve to detect and measure the PET-radiation emitted in the region of the opening 28 of the detector ring 2. The detector ring 2 has the basic shape of a ring in each case, with a non-round inner surface 23 and a circular outer surface 27.

In both embodiments shown in FIGS. 1 and 2, the detector ring 2 is arranged between two holding arms 41 that hold the detector ring 2 between them. The two holding arms 41 form a part of a U-shaped portion 4, which is attached to a main supporting structure 3. The detector ring 2 is rotatable about an axis of rotation R that extends through the two holding arms 41 of the U-shaped portion 4. Furthermore, the detector ring 2 is displaceable together with the U-shaped portion 4 along an inclined displacement direction D relative to the main supporting structure 3 in both embodiments. In order to facilitate rotation and displacement of the detector ring 2, one or several handles can be attached to the outer surface of the detector ring 2. It is, however, also possible that the detector ring 2 is displaceable by means of a motor which can be operated by an operator O via a displacement button 35. The displacement button 35 is preferably arranged at the main supporting structure 3, as shown in FIG. 2.

The direction D along which the U-shaped portion 4 is displaceable is inclined with respect to the direction of gravity G, meaning that it is neither parallel nor perpendicular to the direction of gravity G. In both embodiments of FIGS. 1 and 2, the U-shaped portion 4 is attached to a guide rail 31 that is provided on the main supporting structure 3 and allows the U-shaped portion 4 to be displaced along the inclined displacement direction D as mentioned. Thus, the guide rail 31 also extends along the inclined direction.

The axis of rotation R extends along a horizontal direction, i.e. perpendicularly to the direction of gravity G. Furthermore, the axis of rotation R extends perpendicularly to the direction along which the U-shaped portion 4 can be displaced. The displacement direction D is approximately perpendicular to the longitudinal extension of the holding arms 41.

In the first embodiment shown in FIG. 1, the main supporting structure 3 comprises a lower vertical portion and an upper inclined portion. The U-shaped portion 4 is attached to the upper side of the upper inclined portion of the main supporting structure 3 in such a way, that the U-shaped portion 4 is displaceable along the entire length of the upper inclined portion. The two holding arms 41 of the U-shaped portion 4 serve to hold the detector ring 4 between them. For this purpose, two fixation lugs 21 are attached to the outer surface of the detector ring 2. The fixation lugs 21 are provided on diametrically opposite sides of the detector ring 2. The fixation lugs 21 engage with a through-hole in each of the holding arms 41.

The engagement of each fixation lug 21 and the respective through-hole is such, that a rotation of the detector ring 2 about the axis of rotation R is enabled. The axis of rotation R is defined by the position of the fixation lugs 21. Thus, the axis of rotation R extends centrally through each of the two fixation lugs 21 and through each of the holding arms 41. With regard to the detector ring 2, the axis of rotation R extends diametrically through the ring and preferably through the centre of mass of the detector ring 2.

For carrying out the PET-image acquisition, a computing device 5 is accommodated within the main supporting structure 3. Data and/or energy transmission to or from the computing device 5 can be done via one or several cables and/or wirelessly. In other embodiments, the computing device 5 could also be arranged externally. The computing device 5 is preferably connected, by cable or wirelessly, to a user input and output device. The user input and output device can for example be in the form of an external personal computer or it can be a display, in particular a display with a touch screen, which is attached to the PET-scanning device.

A scanning support 6 is provided for accommodating a human patient in an inclined sitting position during the scanning procedure. The scanning support 6 can be part of the PET-scanning device 1 as in the embodiment of FIG. 2 or can form a separate unit as in the embodiment of FIG. 1. Prior to the image acquisition, the patient is accommodated on the scanning support 6 with the detector ring 2 being in the uppermost position of the main supporting structure 3. The detector ring 2 is then rotated and displaced by the medical personnel into an optimal position for the image acquisition using the handle(s) (not shown in the figures).

The scanning support 6 in the form of a chair-like seating unit comprises a base structure 61 that supports a seat base 62 and a leg support 63 for supporting the legs of the patient during the scanning procedure. Also attached to the base structure 61 is an inclined back support 64. Attached to the upper side of the back support 64 are a backrest 65 and pivotable (see arrow in FIG. 1) armrests 67. The backrest 65 can be displaced along the back support 64 (double arrow in FIG. 1), in order to optimally accommodating the patient during the PET-scanning procedure. At the upper end, a headrest 66 is attached to the backrest 65 in such a way, that a displacement of the headrest 66 along the longitudinal direction of the backrest 65 is possible (double arrow in FIG. 1), in order to further adjust the scanning support 6 to the patient. For the image acquisition, the head of the patient rests on the headrest 66 and the detector ring 2 is displaced and rotated such that the patient's head is arranged within the opening 28 of the detector ring 2. Thus, the headrest 66 is likewise arranged inside of the detector ring 2 during the imaging process.

The displacement direction D of the detector ring 2, which is defined by the longitudinal extension of the guide rail 31 (not shown in FIG. 1) that are attached to the main supporting structure 3, approximately corresponds to the longitudinal extensions of the back support 64 and of the backrest

65 as well as to the directions along which the back support 64 and the backrest 65 are displaceable. Thus, the displacement direction D of the detector ring 2 corresponds to the longitudinal main axis of the upper part of the body of the patient, if the patient sits in the scanning support 6 as intended and is ready for the scanning procedure. In order to prevent the patient from moving his head during the image acquisition, a head strap 68 can be used (see FIG. 9).

In the embodiment of FIG. 1, the scanning support 6 is separate from the rest of the PET-scanning device 1 and in particular from the main supporting structure 3. The main supporting structure 3 of the PET-scanning device 1 comprises a base structure 32, to which wheels 33 are attached. By means of the wheels 33, the PET-scanning device 1 can be moved, in order to bring it to the patient. The scanning support 6 does not have any wheels here. Thus, the location of the scanning support 6 is fixed, which has the advantage that the external parameters and conditions are well-defined and known with regard to the scanning procedure. In such a setting, the PET-scanning device 1 can e.g. be used in combination with one or more such scanning supports 6, in order to use the same PET-scanning device 1 for carrying out PET-scans at several designated locations of e.g. a hospital or a nursing home. Positioning means are preferably provided, that allow the main supporting structure 3 to be positioned in a well-defined, exact and reproducible way with respect to the scanning support 6.

As can be seen from the views of FIGS. 1 and 2, the U-shaped portion 4 and the main supporting structure 3 including the base structure 32 together form a Z-shaped structure in each case. The stability of the PET-scanning device 1 is optimized by this shape.

From the main supporting structure 3, the two holding arms 41 of the U-shaped portion 4 extend in parallel in an obliquely upward direction with respect to the direction of gravity G. During the acquisition of PET-scanning images, the head of the patient is located within the opening 28 of the detector ring 2 and, thus, in the area between the two holding arms 41.

For viewing the obtained tomographic images, a screen 34 can be attached to the main supporting structure 3, as shown in FIG. 2. The screen 34 serves to display one or more projection views of the patient's head. Using the displacement button 35, the operator O can position the patient in such a way, that the part of the body, in particular the brain, of the patient that is to be examined is positioned within the field-of-view of the PET-scanning device 1, that is to say preferably as close to the center of the detector ring 2 as possible.

The screen 34 and/or the displacement button 35 can of course also be arranged distantly to the main supporting structure 3. They can for example be part of a remote computer station that serves to control the PET-scanning device 1 or they can be formed by e.g. a smart phone or an external tablet device.

Figure 3:
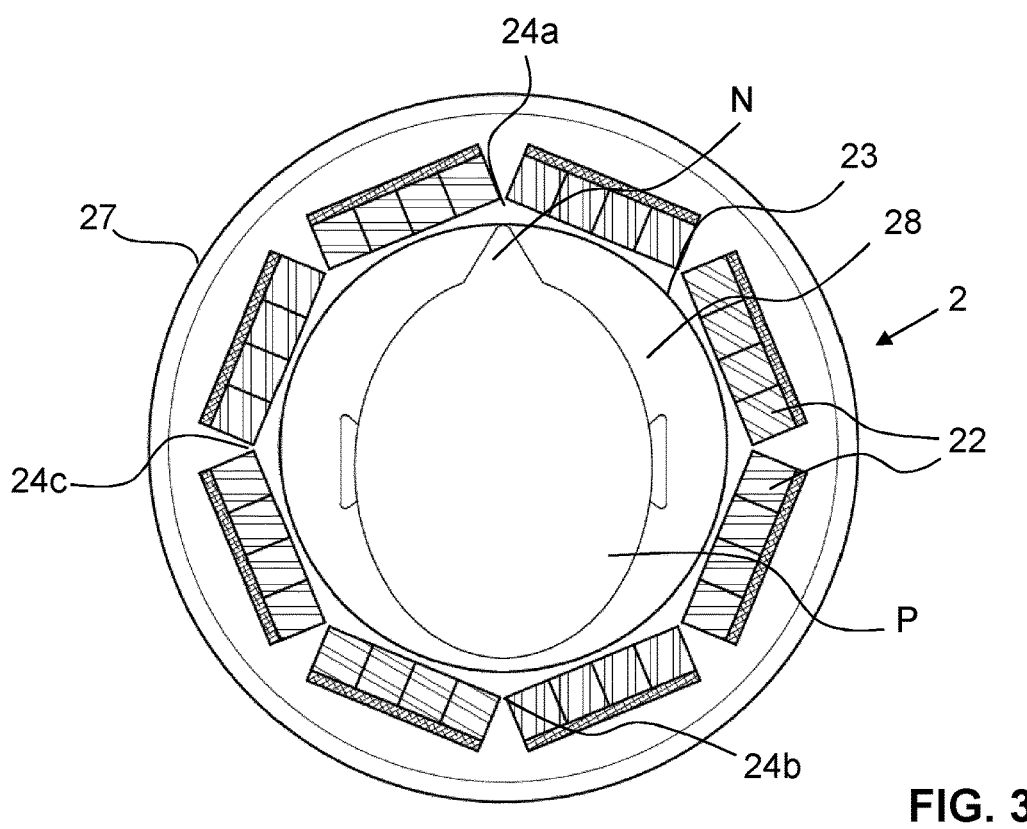
FIG. 3 shows a schematic cross-sectional view through the detector of a PET-scanning device according to a non-inventive embodiment, with a patient's head accommodated in the detector's opening.

FIG. 3 shows a cross-sectional view through a detector ring 2 of a PET-scanning device 1 according to a non-inventive embodiment. The detector ring 2 has the design of a closed ring with a circular inner surface 23 and a circular outer surface 27. The inner surface 23 and the outer surface 27 are both part of a housing of the detector 2 that accommodates a plurality of sensor modules 22 in its inside. The sensor modules 22 serve to detect PET-radiation that is emitted from the head of a patient P that is accommodated within the opening 28 of the detector 2. For this purpose, the sensor modules 22 are all directed with their flat detector surfaces towards the center of the opening 28. The sensor modules 22 are connected to the computing device 5. In the present embodiment, there are eight sensor modules 22, which are arranged in the form of an octagon, i.e. of a regular polygon.

As can be seen from FIG. 3, the circular shape of the inner surface 23 is not optimally with respect to the usual elongated transversal shape of the human head. In order to minimize the distance of the sensor modules 22 to the head of the patient P, the diameter of the circular inner surface 23 needs to be minimized. This, however, leads to the situation as shown in FIG. 23, where the nose N of the patient P almost touches the inner surface 23. Thus, the possible minimum distance between the sensor modules 22 and the patient's head is limited by the maximum transversal extension of the patient's head, which is given by the distance between the tip of the nose N and the back of the head. It also needs to be considered that the situation as shown in FIG. 3 with the nose N almost touching the inner surface 23 is uncomfortable for most of the patients P. As a result, the diameter of the inner surface 23 needs to be chosen even somewhat larger than as shown in FIG. 23, which means that the sensor modules need to be positioned further outwards.

Figure 4:
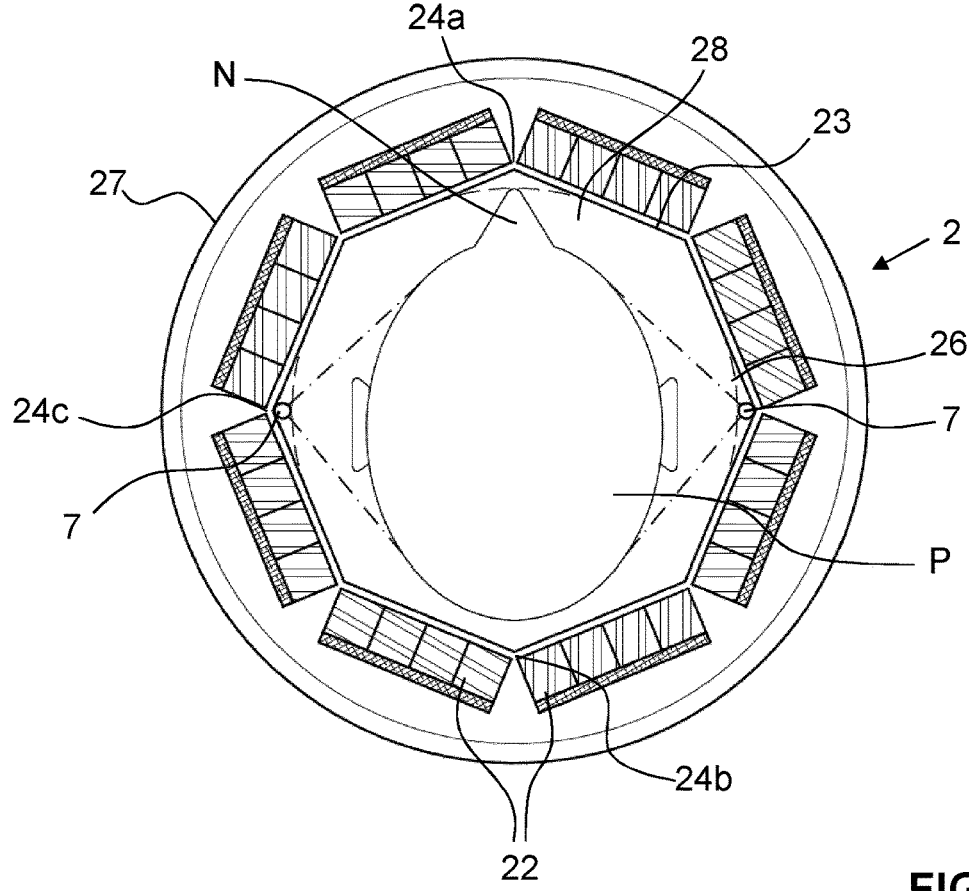
FIG. 4 shows a schematic cross-sectional view through the detector of a PET-scanning device according to a first inventive embodiment, with a patient's head accommodated in the detector's opening.

FIG. 4 shows a first embodiment of an inventive detector ring 2, which differs from the embodiment of FIG. 3 in the shape of the inner surface 23. In particular, the shape of the inner surface 23 here corresponds to the one of the polygon which is formed by the octagonal arrangement of the sensor modules 22. In other words, the inner surface 23 also forms an octagon in the transversal view. Since the sensor modules 22 are arranged such that one of the corners of the polygon is arranged in the immediate region of the patient's nose N, more space is given for the patient, if the polygonal shape is reflected by the inner surface 23. The corner of the polygon, which is arranged in the region of the nose N, serves to accommodate the nose N and, therefore, can be referred to as the nose corner 24a. The corner which is arranged diametrically opposite of the nose corner 24a can be referred to as the headrest corner 24b. It serves to accommodate the back of the patient's head. As can be seen by comparing FIGS. 3 and 4, there is considerably more space for the patient P within the detector 2 according to the inventive embodiment of FIG. 4. Since the shape of the inner surface 23 corresponds to the shape of how the sensor modules 22 are arranged, the space of the opening 28 is maximized.

As can also be seen from FIG. 4, two of the corners, which are referred to as ear corners 24c, are arranged in the immediate regions of the patient's ears. The ear corners 24c thus serve to accommodate the patient's ears. The position of the ear corners 24c is also optimal to accommodate a laser positioning device 7, which serves to project a line onto the head of the patient P (see the dash dotted lines illustrating the laser light, in this respect). With the help of this line, the operator of the PET-scanning device 1 can correctly position the patient P in the PET-scanning device 1.

The two corners which are located between the nose corner 24a and each of the ear corners 24c are arranged in the regions of the patient's eyes. Particularly the enlargement of the space in these regions as compared to the embodiment of FIG. 3 makes the patient P to be more comfortable.

In a combined view of e.g. FIGS. 2 and 4, the detector ring 2 is preferably attached such to the U-shaped portion 4 that the headrest corner 24b represents the corner of the polygon that is arranged closest to the main supporting structure and, during the PET-scanning procedure, accommodates the headrest 66. The axis of rotation R preferably extends through the ear corners 24c. As a result of this attachment of the detector ring 2 to the main supporting structure 3, the patient will automatically take a position in the PET-scanning device 1 that, during the scanning procedure, his nose N is accommodated in the nose corner 24a.

FIGS. 5 to 7 show further embodiments of an inventive detector 2 with four sensor modules 22 arranged in a square (FIG. 5), with five sensor modules 22 arranged in a pentagon (FIG. 6) and with six sensor modules 22 arranged in a hexagon (FIG. 7).

As can be seen from FIGS. 5 to 7 (and 4), the space to accommodate the patient's nose N is particularly large, if the arrangement of the sensor modules 22 results in a polygon with less corners. On the other hand, if the polygon has more corners, the sensor modules 22 become smaller and are directed with a larger section of their detector surface towards the center of the opening 28. The embodiments with a pentagon having an even number of corners have the advantage that there is a headrest corner 24b.

The shape of the inner surface 23 can correspond to the polygonal shape that is formed by the sensor modules 22, in order to maximize the opening 28. It is, however, also possible that the inner surface 23 describes a curvature that corresponds to the incircle 26 of the polygon in the areas of some of the corners, as it is illustrated in FIGS. 5-7 by dashed lines. Thus, the inner surface 23 has rounded corners 25. In this way, the inner surface 23 has a smooth and rounded design.

Figures 8, 9:
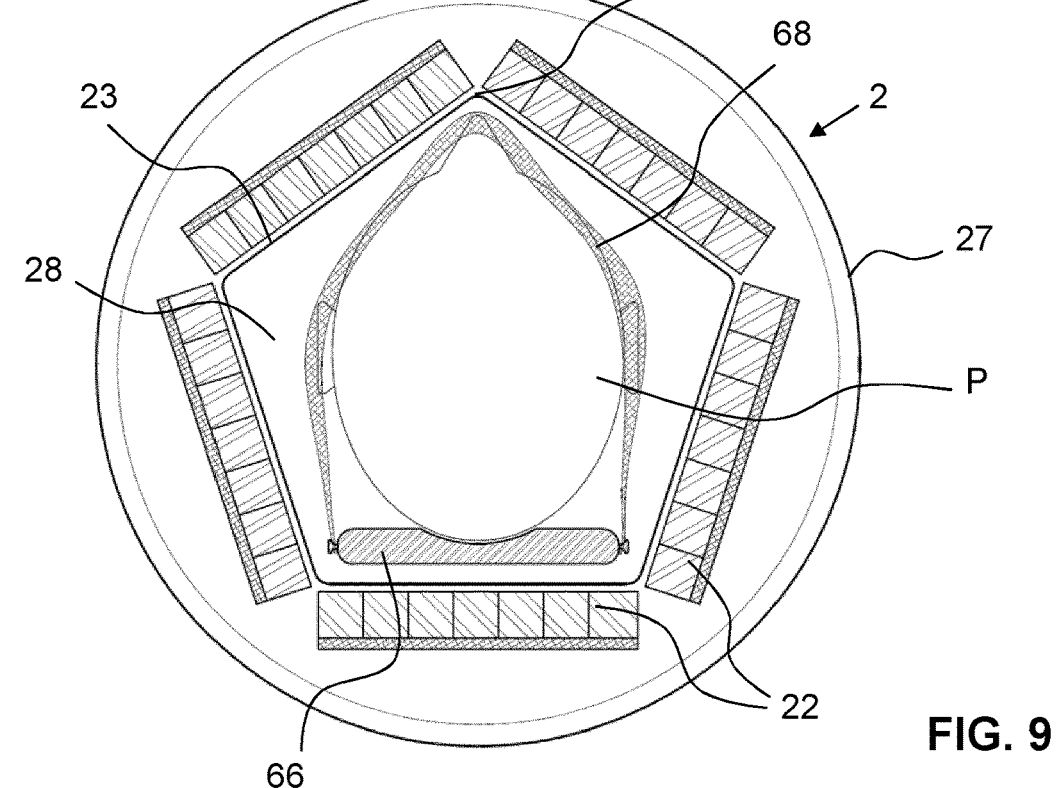
FIG. 8 shows a schematic cross-sectional view through the detector of a PET-scanning device according to a fifth inventive embodiment, with a patient's head accommodated in the detector's opening.
FIG. 9 shows a schematic cross-sectional view through the detector of a PET-scanning device according to a sixth inventive embodiment, with a patient's head accommodated in the detector's opening by means of a head strap.

FIG. 8 shows a particularly preferred embodiment, in which the sensor modules 22 are arranged in the form of an octagon. The inner surface 23 reflects the shape of the octagon particularly in the regions of the nose corner 24a and of the headrest corner 24b, in order to maximize the opening 28 in these regions. The space of the ear corners 24c is used to accommodate a laser positioning device 7 in each case. The laser positioning devices 7 can be arranged radially inside of the inner surface or, as it is the case here, outside of the inner surface 23. In the latter case, the inner surface 23 can comprise transparent windows, in order to let pass the laser light. As can be seen in FIG. 8, the inner surface 23 is flattened in the regions of the ear corners 24c. In the corners between the nose corner 24a and the ear corners 24c and between the headrest corner 24b and the ear corners 24c, thus in every second corner, the inner surface 23 describes a curvature that corresponds to the incircle 26 of the octagon. At the nose corner 24a and the headrest corner 24b, the inner surface 23 likewise forms a corner that is slightly rounded. Thus, the inner surface 23 has a smooth, rounded design along of its entire circumference, while at the same time offering a large opening 28 to accommodate the head of the patient P.

The minimum diameter of the opening 28 is indicated by a dashed line in FIG. 8 and is preferably approximately 260 mm.

FIG. 9 shows an inventive embodiment of a detector 2 having a pentagonal arrangement of sensor modules 22. The inner surface 23 also forms a pentagon and, thus, reflects the arrangement of the sensor modules 22 along of its entire circumference. The detector 2 of FIG. 9 is applied for PET-imaging in relation to stereotactic surgery. For this purpose, the head of the patient P is attached to the headrest 66 by means of a head strap 68, in order to achieve high accuracy with respect to the medical instruments used in the surgery. As can be seen from FIG. 9, the pentagonal shape of the inner surface 23 is here advantageous to accommodate the headrest 66.

The present invention is of course not limited on the embodiments as described and as shown in FIGS. 1 to 9. The elements presented and described with respect to FIGS. 1 to 12 can of course be exchanged and combined and many modifications are possible. Features that have been indicated with respect to certain embodiments only, can well be provided in other embodiments, too. For example, the outer surface 27 could also have polygonal or any other shape in each embodiment. The PET-scanning device 1 does not necessarily have to be a brain scanner, but could also be a whole-body scanner for example. The polygonal arrangement of the sensor modules which is reflected by the inner surface at least in the region of the nose is also advantageous for whole-body scanners due to the same reasons as described, in particular because these scanners are also often used for brain scanning. A plurality of further modifications is possible.

The invention claimed is:

1. A detector for a positron emission tomography (PET)-scanning device, the detector comprising an opening sized to accommodate the head of a human patient;

a plurality of sensor modules, which serve to detect emitted PET-radiation from the human patient and are arranged in the form of a regular polygon having a plurality of corners; and an inner surface, which is arranged radially inside of the sensor modules, in order to circumferentially delimit the opening, wherein the sensor modules are arranged such that one of the corners is a nose corner which is adapted to accommodate the patient's nose when the patient's head is positioned in the opening of the detector in order to be scanned by the PET-scanning device, and wherein the inner surface reflects the shape of the polygon at least in a region of the nose corner, and wherein the inner surface defines a curvature that corresponds to the incircle of the polygon in areas of one or more of the plurality of corners.

2. The detector according to claim 1, wherein the polygon has twelve corners or less.

3. The detector according to claim 2, wherein the polygon has eight corners or less.

4. The detector according to claim 1, wherein the polygon has an even number of corners.

5. The detector according to claim 1, wherein the inner surface also reflects the shape of the polygon in a region which is arranged diametrically opposite of the nose corner.

6. The detector according to claim 1, wherein the inner surface also reflects the shape of the polygon in immediate regions where the ears of the patient would be positioned when the patient's head is positioned in the opening of the detector in order to be scanned by the PET-scanning device.

7. The detector according to claim 1, wherein the polygon is an octagon.

8. The detector according to claim 1, wherein the polygon is an octagon, and wherein the inner surface describes a curvature that corresponds to the incircle of the polygon in the areas of every second of the plurality of corners, starting with a corner being arranged adjacent to the nose corner.

9. The detector according to claim 1, wherein one sensor module is assigned to each side of the polygon.

10. The detector according to claim 1, additionally comprising one or more laser positioning devices, each of which is arranged in a different corner of the plurality of corners of the polygon.

11. The detector according to claim 1, comprising a headrest that is adapted to be accommodated in a region of the opening which is arranged diametrically opposite of the nose corner.

* * * * *